April 27, 1943. J. S. ELLIOTT Plant Pat. 579
ROSE PLANT
Filed Dec. 7, 1942
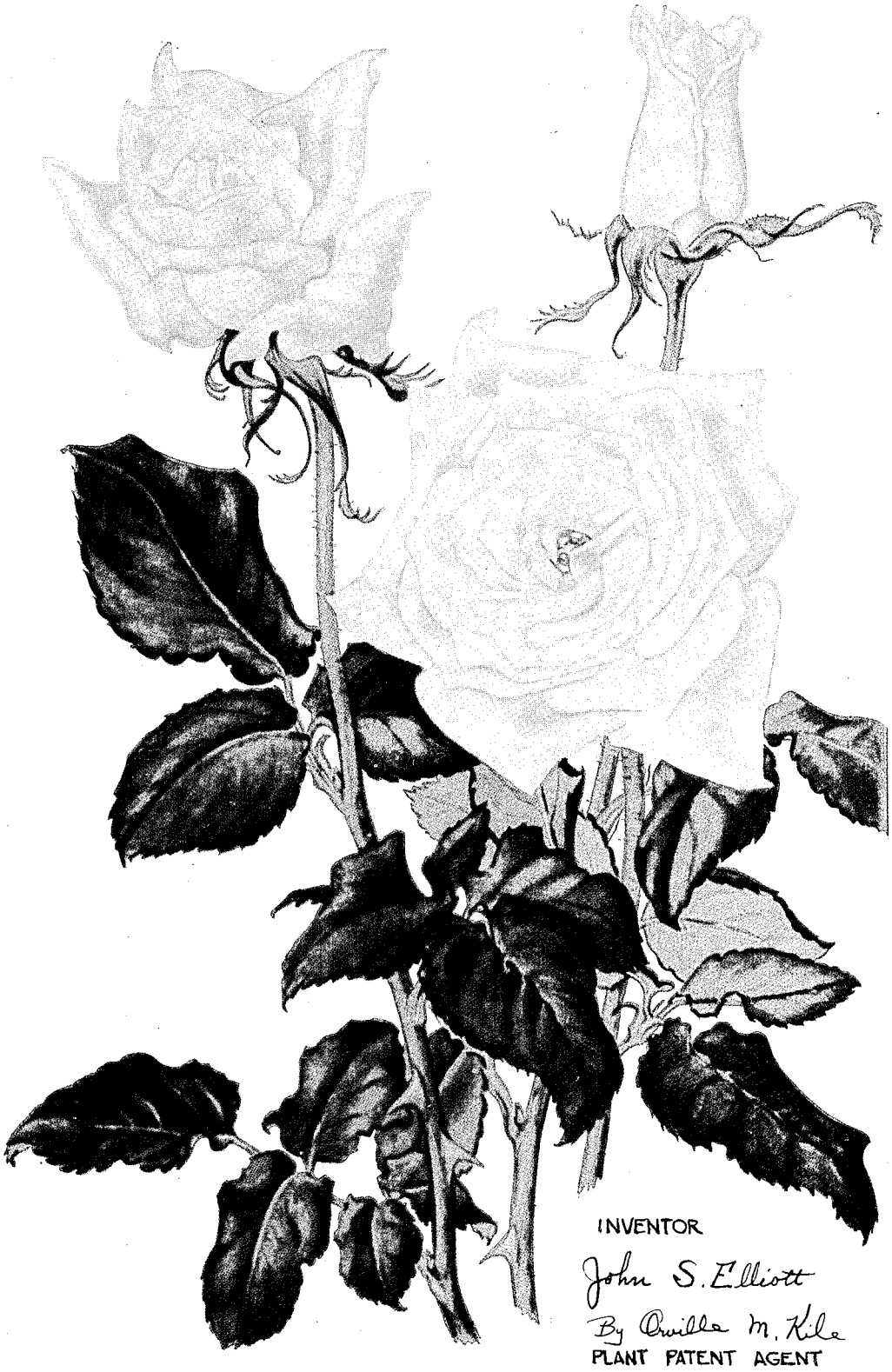

Patented Apr. 27, 1943

Plant Pat. 579

UNITED STATES PATENT OFFICE

579

ROSE PLANT

John S. Elliott, Madbury, N. H.

Application December 7, 1942, Serial No. 468,133

1 Claim. (Cl. 47—61)

My present discovery relates to improvements in hybrid tea rose plants designed particularly for hothouse culture but also adaptable to outdoor growing. The improvement consists principally in the combination of blossoms of lovely delicate yellow color and excellent high-centered form, with a plant of great vigor and prolific production of high quality flowers. No other such combination exists in flowers of known varieties.

My new variety originated as a sport of the variety Token, which is the subject of Plant Patent No. 95. It was discovered by me in my greenhouse at Dover, New Hampshire. It has been asexually reproduced and its features appear to be firmly fixed.

The accompanying illustration shows, in the original, three specimens of the flower in full color and in various stages of opening, together with portions of the stems and foliage.

Following is a detailed description of the flower and plant of this new variety. Color plate references indicate Ridgway's Color Standards and Nomenclature. Where plate references are not given, ordinary dictionary meanings are intended.

*The plant*

Form: Upright bush. Usual height 3½ to 4 feet.

Growth: Very vigorous. Similar to but not identical with that of its parent.

Blooming habit: Prolific producer of high quality flowers. Has a higher percentage of production of heavy, high standard flowers of commercial quality than any other known yellow variety.

Foliage: Heavier and darker and somewhat different in form from that of the parent variety.

*Leaflets.*—Three to five.

*Quantity.*—Abundant.

*Size.*—Large.

*Texture.*—Substantial; somewhat leathery.

*Appearance.*—Only slightly glossy on upper surface. Under surface dull.

*Shape.*—Elliptical with sharp apex and rounded base.

*Edge.*—Very finely serrated.

*Color.*—Upper surface deep rich green, approximately Dark Dull Yellow Green (Pl. XXXII) in shade. Under surface approximately Light Elm Green (Pl. XVII), with occasional reddish tinge. Midribs tinged with red.

Rachis: Smooth below, deeply grooved above. Light green in color.

Stipules: Narrow; clinging; long-pointed.

Stems: Approximately Parrot Green (Pl. VI). Erect and heavy. Moderate number of thorns.

*Thorns.*—Hooked downward; usually greenish white with red tinge.

*The flower*

Bud:

*Size.*—Large, about 2 inches long before beginning to unfurl.

*Shape.*—At first a long slender bud, later somewhat urnshaped.

*Color.*—Delicate but very clear yellow. The color lies between Pale Lemon Yellow (Pl. IV) and Pinard Yellow (Pl. IV), with base and veining approximately Wax Yellow (Pl. XVI). Edge of petals approximately Straw Yellow (Pl. XVI). Veining rather prominent.

*Sepals.*—Fringed and somewhat foliaceous. Reflex when bud begins to unfurl.

*Opening.*—Opens very slowly and perfectly.

*Peduncle.*—Short (3 to 4½ inches), bringing foliage close to blossom; beset with many spines; same color as stems.

Blossom:

*Size.*—Large, about 4½ inches in diameter.

*Form.*—When first open it is high-centered, with frame of five loosely arranged petals. The petals then begin to roll backward slightly in triangular shape (particularly the outer petals), making the flower somewhat star-shaped. A little later the flower opens into a deep cup shape, disclosing a large number of stamens and pistils.

*Color.*—When the flower is half open, the general color effect is an all-over color between Strantian Yellow and Wax Yellow (Pl. XVI), surrounded by a row of lighter petals approximately Barium Yellow (Pl. IV) on the edge and with a large base of Strontian Yellow (Pl. XVI) extending up into the veins.

The inner petals are much darker in tone than the outer ones, particularly on their edges.

The full-blown rose appears to be a much deeper yellow (between Amber Yellow and Wax Yellow, Pl. XVI), because more of the darker inner surface of the petals is visible. The effect of color depth is increased because of the many stamens with very large anthers approximately Light Cadmium (Pl. IV). Although there is this appearance of deepening of color, there is scarcely any actual change of color during the entire life of the flower.

*Fragrance.*—Delicate and lovely fragrance containing a suggestion of lemon.

*Petalage.*—Average number of petals in October is 25, not including small petaloids. Although the number of petals is not large, they are so arranged and of such substance as to give the appearance of a large rose.

*Petals.—Shape*—outer petals almost round; others slightly narrower. The rolling of the petal edges gives them a triangular appearance. *Size*—outer petals approximately 2½ by 2¼ inches. *Texture*—medium in weight. *Appearance*—silky. *Persistence*—cling until the flower dies. *Lasting quality*—exceptionally long-lasting both as cut flower and on bush. Flowers received in Washington, D. C., on Wednesday, October 21, were many of them still in bud on Saturday, October 24, and some of the flowers lasted until October 31, despite the fact that they had been carried from place to place several times without having their stems in water.

*Reproductive Organs. — Pistils* — many; bunched. *Styles*—white; slender; short. *Stigmas*—red-tinted; topped with white. *Ovaries*—inclosed. *Stamens* — numerous; loosely bunched about pistils. *Filaments*—uneven lengths; Wax Yellow (Pl. XVI) at top, Light Cadmium (Pl. IV) at base. *Anthers*—large; Light Cadmium (Pl. IV).

*Comparisons*

The rose variety which is nearest like my new variety is Pernet, although the similarity is mostly in the color and form of the flower. It differs greatly in growth and type of foliage, as well as in other features. Some differences are enumerated below:

1. The new variety lacks the very glossy leaf appearance of the Pernet.
2. The stems of Pernet are very much thornier than those of the new variety.
3. Pernet lacks the vigor of growth of my new variety.
4. My new variety is a more prolific producer of flowers.
5. The percentage of production of heavy, high-quality flowers is much greater in my new variety.
6. The form and texture of the leaves is different in the two varieties.

Gloria is another variety somewhat similar to my new variety in growth, but it differs principally in the following respects:

1. The flowers of the two varieties differ in form—my new variety being more pointed and star-shaped.
2. The color tone of the flowers differs greatly—my variety being a much more delicate and lighter tone of yellow.
3. The foliage differs in shape, appearance and texture—my new variety having foliage which is darker and more rounded and of thicker texture than that of Gloria.
4. The foliage of my variety is more closely spaced and therefore more abundant than that of Gloria.
5. Although my new variety is prolific in its production of flowers, Gloria is more prolific. Yet my new variety produces a much greater percentage of high quality flowers.
6. My new variety has much heavier and more erect flower stem than Gloria has.

From the above it will be noted that my new variety has in combination the following desirable features—a new combination in roses.

1. Vigorous growth.
2. Prolific production of flowers.
3. High percentage of good flowers.
4. Long, graceful bud.
5. Abundant foliage of good substance and good appearance.
6. Heavy, erect flower stems.
7. Large flowers of exquisite form and delicate color not found in any other known yellow rose.
8. Delicate and distinctive fragrance.
9. Excellent lasting qualities.

Having thus disclosed my discovery, I claim:

The new and distinct variety of hybrid tea rose plant herein disclosed, characterized particularly by its vigorous growth; its prolific flower production; the high percentage of high-quality flowers produced; its heavy, erect flower stems; its abundant and substantial dark green foliage; and the outstanding combination of good form, pleasing fragrance and delicate clear yellow color of its flowers which last exceptionally well.

JOHN S. ELLIOTT.